United States Patent [19]

Ito

[11] Patent Number: 4,972,828

[45] Date of Patent: Nov. 27, 1990

[54] ENDOSCOPE HAVING ADJUSTABLE FORCEPS INSERTION INLET PORTION

[75] Inventor: Keiji Ito, Tokyo, Japan

[73] Assignee: Asahi Kogaku Kogyo Kabushiki Kaisha, Tokyo, Japan

[21] Appl. No.: 331,982

[22] Filed: Apr. 3, 1989

[30] Foreign Application Priority Data

Apr. 25, 1988 [JP] Japan .............................. 63-55793[U]

[51] Int. Cl.⁵ .............................................. A61B 1/00
[52] U.S. Cl. ...................................................... 128/4
[58] Field of Search ...................................... 128/4, 6, 7

[56] References Cited

U.S. PATENT DOCUMENTS 4,705,023  11/1987  Arai ........................................... 128/4
4,750,477   6/1988  Wardle ....................................... 128/4

FOREIGN PATENT DOCUMENTS 2946372  12/1982  Fed. Rep. of Germany .
3616615   4/1988  Fed. Rep. of Germany .
51-69392   6/1976  Japan .
61-265125 11/1986  Japan .

Primary Examiner—William H. Grieb
Attorney, Agent, or Firm—Sughrue, Mion, Zinn, Macpeak & Seas

[57] ABSTRACT

An endoscope which is convenient to use to both right- and left-handed individuals. The endoscope has a connection portion extending between an operating portion and an insertion portion which is sheathed with a cylindrical sheath casing having a forceps insertion inlet projecting therefrom. The sheath casing is capable of being axially rotated so as to change the direction thereof and being held in a fixed position after being rotated to the desired position.

8 Claims, 5 Drawing Sheets

# ENDOSCOPE HAVING ADJUSTABLE FORCEPS INSERTION INLET PORTION

BACKGROUND OF THE INVENTION

The present invention relates to an endoscope. More particularly, the invention relates to an endoscope having an improved structure in the region of a forceps insertion inlet.

In recent endoscopes, the connection portion extending between the operating portion and the insertion portion of the endoscope is sheathed with a cylindrical sheath casing. A forceps insertion inlet projects from the connection portion. The forceps insertion inlet is generally fixed in a single direction considered optimum taking into account the manner in which the endoscope is to be used.

A right-handed person will generally grasp the operating portion with his or her left hand while performing the actual forceps inserting or removing operation with the right hand. However, a left-handed person will usually grasp the operating portion with the right hand and perform the actual forceps inserting or removing operation with the left hand. Accordingly, an endoscope which is easy to use for a right-handed person may not always be equally easy to use for a left-handed person. It is therefore necessary for the manufacturer to offer two versions of endoscopes differing from one another only in the direction of the forceps insertion inlets, namely, one version for right-handers and another for left-handers. This is of course expensive.

As a compromise, manufacturers of endoscopes generally offer in Japan, where left-handedness is societally discouraged, only right-handed versions, whereas in occidental countries, where left-handed persons form a larger percentage of the population, endoscopes are sold in which the forceps insertion opening is disposed at a middle position between the optimum positions for right- and left-handers. Still, however, two endoscopes differing from one another only in this feature must be carried in the product line, which is yet uneconomical.

SUMMARY OF THE INVENTION

It is, therefore, an object of the present invention to eliminate the above problem in the endoscope manufacturing art, and to provide endoscopes in which versions differing from one another in the direction of the forceps insertion inlet can be produced at less cost.

In accordance with this and other objects of the invention, there is provided an endoscope having a connection portion extending between an operating portion and an insertion portion which is sheathed with a cylindrical sheath casing having a forceps insertion inlet projecting therefrom, in which the sheath casing is capable of being axially rotated so as to change the direction thereof and being held in a fixed position after being rotated to the desired position. Thus, the direction of the forceps insertion inlet can be set to optimally suit either a right-handed or left-handed individual.

DESCRIPTION OF THE PREFERRED EMBODIMENTS

Figure 1:
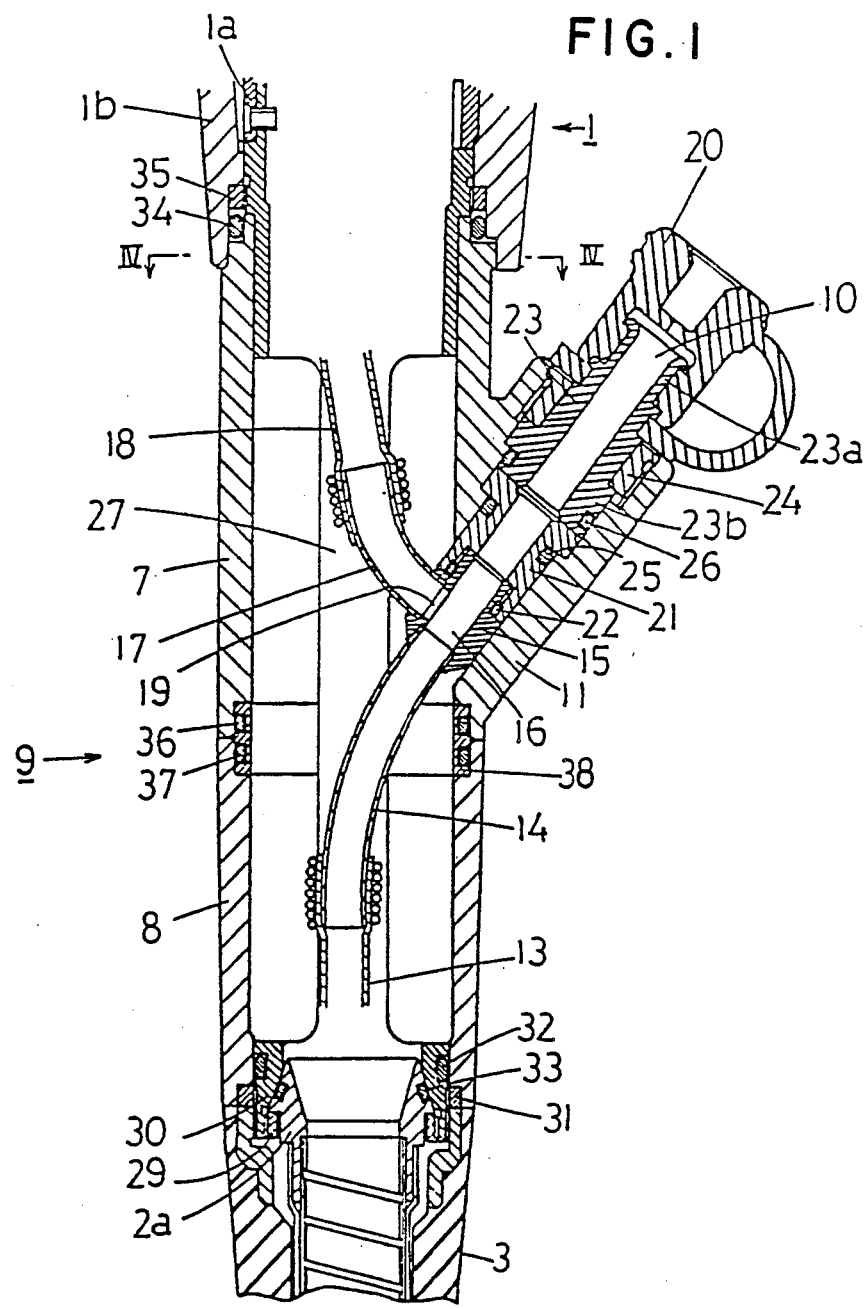
FIG. 1 is a side sectional view showing the region around a connection portion of an endoscope constructed in accordance with a first preferred embodiment of the invention.

Referring to the drawings, preferred embodiments of endoscopes constructed in accordance with the teachings of the present invention will be described.

Figure 2:
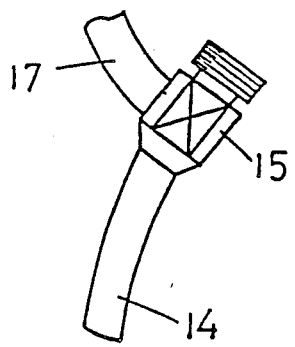
FIG. 2 is a side view showing the whole of the endoscope of the first embodiment.

FIG. 2 is an external view showing an endoscope of a first embodiment of the invention. In this drawing, reference numeral 1 designates an operating portion, 2 indicates a flexible insertion portion, and 3 designates a tapered rubber bending-restraining portion attached to the base of the insertion portion 2. A bending portion 4 which is capable of being bent through remote manipulation is formed at the forward end of the insertion portion 2, and a bending operating (manipulating) lever 5 is provided on the operating portion 1. Reference numeral 6 designates a suction operation valve.

A connection portion 9, sheathed with cylindrical sheath casings 7 and 8, is formed between the operating portion 1 and the insertion portion 2, and a forceps insertion inlet 10 is projectingly provided on the first sheath casing 7. Reference numeral 11 denotes a projecting portion of the forceps insertion inlet 10. The sheath casings 7 and 8 are made of a synthetic resin and are formed, for example, by injection molding. Reference numeral 13 designates a forceps channel which opens at the forward end of the insertion portion 2 and is constituted by a tube made, for example, of polytetrafluoroethylene.

Figure 3:
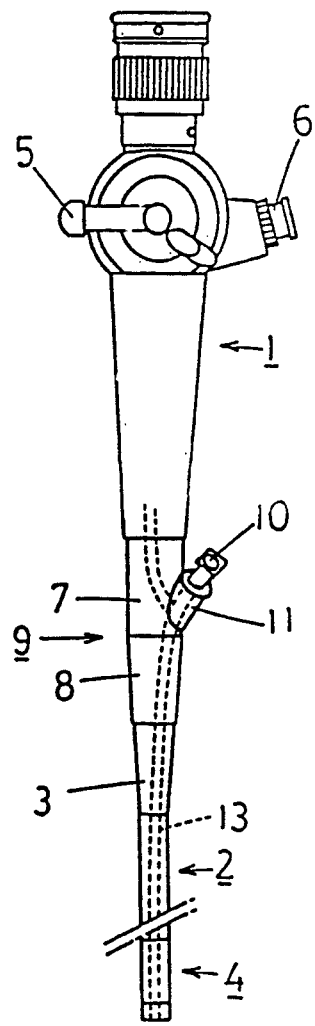
FIG. 3 is a side view of a branch block of the endoscope of the first embodiment.

FIG. 1 shows a cross-sectional view of the vicinity of the connection portion 9. The base end portion of a forceps channel 13 is connected through a stainless steel pipe 14 to a branch block 15 as shown also in FIG. 3. A forceps insertion orifice 16 communicating directly with the pipe 14 and a suction pipe orifice 19, which branches from the branch block 15 in a sideward direction and communicates with a suction device (not shown) through a coupling pipe 17 and a suction tube 18, are formed on the branch block 15.

The branch block 15 is disposed inside the base portion of the projecting portion 11 formed on the first sheath casing 7. The branch block 15 has a flattened cylindrical shape formed by cutting away opposed side portions of a cylindrical member. An engagement portion which engages the branch block 15 is formed at the base portion of the projecting portion 11 of the sheath casing which engages the branch block 15 to prevent the latter from rotating.

Reference numeral 21 designates a fastening ring made, for example, of stainless steel, which is threadedly engageable with the branch block 15 in such a manner that when the fastening ring 21 is threadedly engaged with the branch block from the upper side of the latter, the branch block 15 is drawn against the fastening ring 21 and fixed in the state shown in FIG. 1. Reference numeral 22 denotes an 0-ring provided for sealing purposes.

Further, reference numeral 23 designates a forceps insertion mouthpiece fixed by means of a nut 24 at an upper portion of the projecting portion 11. The mouthpiece 23 may, for example, be made of stainless steel. A forceps cap 20 made of rubber or synthetic resin is removably attached to a head portion 23a of the forceps insertion mouthpiece 23. A collar portion 23b of the forceps insertion mouthpiece 23 has a noncircular form in cross section so as to be prevented from rotating when it is fitted in the projecting portion 11. Reference numerals 25 and 26 indicate O-rings provided for sealing purposes.

Reference numeral 27 designates a frame for connecting the operation portion 1 to a mouthpiece 2a on the base end of the insertion portion. An upper end portion of the frame 27 is fixed to a frame 1a of the operating portion by a screw, and a socket 30 for fastening and fixing the mouthpiece 2a of the insertion portion with a nut 29 is fixed to a lower end portion of the frame 27. A nut 31 screwed onto the socket 30 presses the two sheath casings 7 and 8 against the bottom portion of a sheath cover 1b of the operating portion so as to hold the sheath casings in place. Reference numerals 32, 33 and 34 designate sealing O-rings. Reference numeral 35 indicates a nut fixing the sheath cover 1b of the operating portion. A connecting ring 38 to which sealing O-rings 36 and 37 are attached is interposed between the two sheath casings 7 and 8 at the junction area therebetween so as to prevent the entry of water.

Figure 4:
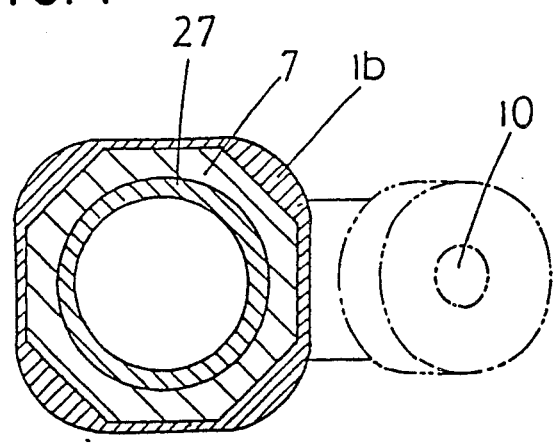
FIGS. 4 through 7 are cross-sectional views showing the set direction of the forceps insertion opening inlet of the endoscope of the first embodiment in various positions.

FIG. 4 illustrates the connecting portion between the first sheath casing 7 and the sheath cover 1b of the operating portion. In accordance with the present invention, the first sheath casing 7 and the sheath cover 1b of the operating portion have end portions which are a regular octagonal shape in cross section and which are dimensioned to fit together in that area. Although the case is illustrated where the first sheath casing 7 is fitted inside the sheath cover 1b of the operating portion, the opposite case may be employed, that is, the sheath cover 1b may be fitted inside the first sheath casing 7.

As shown in FIG. 4, the forceps insertion inlet 10 is fixed in the position in which the forceps insertion inlet 10 faces the front of the endoscope (to the right in the drawing). This position may make the endoscope not so easy to use for both right- and left-handed persons. However, the orientation of the forceps insertion inlet 10 can readily be changed by means of the fixing nut 31. That is, due to the provision of the interfitting regular-octagonal end portions of the first sheath casing 7 and the sheath cover 1b of the operating portion, the first sheath casing can be rotated in steps of 45 degrees relative to the sheath cover 1b of the operating portion before the former is fixed to the latter. That is, the first sheath casing 7 can be fixed to the sheath cover 1b at a desired angle by means of the nut 31.

Figure 5:
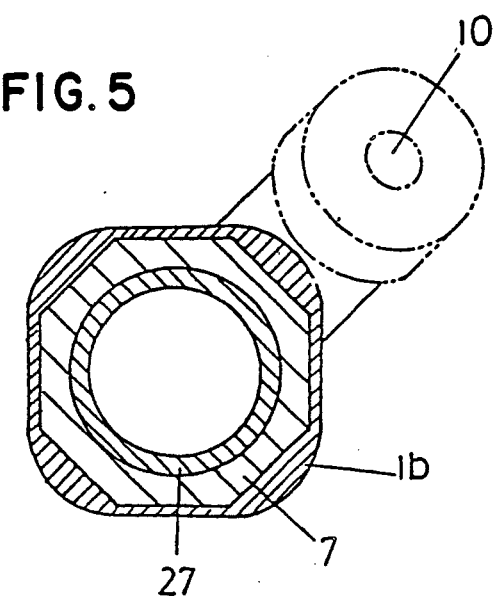
Figure 6:
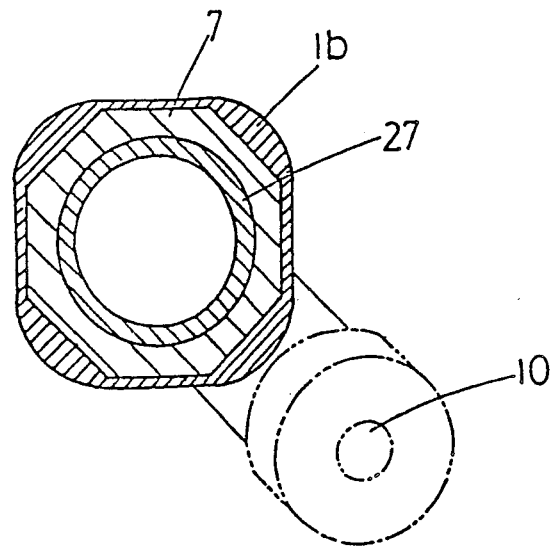
Figure 7:
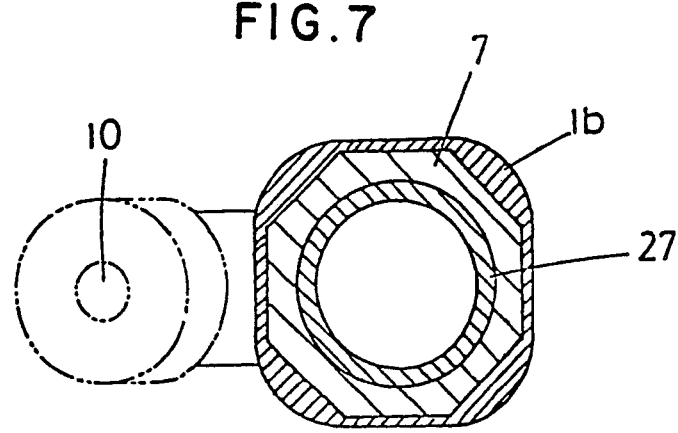

FIGS. 5 through 7 illustrate various positions of the forceps insertion inlet 10. FIG. 5 show the state in which the forceps insertion inlet 10 is rotated counterclockwise by 45 degrees and fixed in that position, as is convenient for a left-handed individual. FIG. 6 illustrates the state where the forceps insertion inlet 10 is rotated clockwise by 45 degrees so as to be convenient for a right-handed user. Further, as shown in FIG. 7, the forceps insertion inlet 10 can be fixed in the opposite direction (rotated by 180 degrees) so as to make the endoscope convenient to use for one who prefers to handle the endoscope while grasping the operating portion 1 in the reverse direction.

Thus, merely by loosening the fixing nut 31, the direction of the forceps insertion inlet can be easily changed. Therefore, the endoscope of the present invention can easily be made convenient to use for all individuals.

Figure 8:
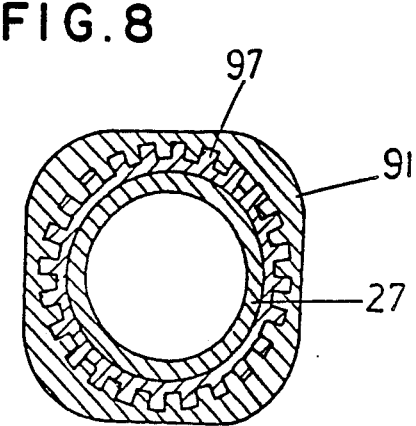

FIG. 8 illustrates a second embodiment of the invention in which respective connecting portions of a first sheath casing 87 and a sheath cover 81 of an operating portion have the shape of a regular dodecagon. In this case, the orientation of the forceps insertion inlet can be changed in steps of 30 degrees.

Figure 9:
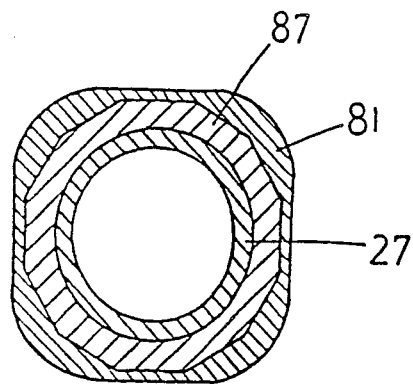
FIGS. 8 and 9 are cross-sectional views of respective second and third embodiments of the invention.

FIG. 9 shows a third embodiment in which the respective connecting portions of a first sheath casing 97 and a sheath cover 91 of the operating portion are splined. The orientation of the forceps insertion inlet can be changed in small angular steps in this case.

Thus, because in the inventive endoscope the orientation of the forceps insertion inlet can be easily changed and fixed at the desired position, the endoscope can be equally conveniently used by right- and left-handed individuals. No change in parts is needed to change the orientation of the forceps insertion inlet. Hence, the cost of the endoscope can be significantly reduced.

What is claimed is:

1. In an endoscope having an operating portion, an insertion portion, a sheath casing sheathing a portion between said operating portion and said insertion portion, and a forceps insertion inlet projecting from said sheath casing, the improvement comprising means for rotatably mounting said sheath a casing with respect to said operating portion and fixing said sheath casing so that said forceps insertion inlet is oriented at a desired angle, said mounting and fixing means comprising interfitting end portions of said sheath casing and operating portion.

2. The endoscope of claim 1, wherein said end portions have the shape of a regular polygon.

3. The endoscope of claim 2, wherein said regular polygon is a regular octagon.

4. The endoscope of claim 3, wherein said regular polygon is a regular dodecagon.

5. The endoscope of claim 1, wherein said interfitting end portions are splined.

6. The endoscope of claim 1, wherein said mounting and fixing means further comprises a nut for fixing said sheath casing and operating portion in position.

7. In an endoscope having an operating portion, an insertion portion, a sheath casing sheathing a portion between said operating portion and said insertion portion, and a forceps insertion inlet projecting from said sheath casing, the improvement comprising means for rotatably mounting said sheath casing with respect to said operating portion and securely fixing said sheath casing to aid operating portion so that said forceps insertion inlet is oriented at a desired angle.

8. In an endoscope having an operating portion, an insertion portion, a sheath casing sheathing a portion between said operating portion and said insertion portion, and a forceps insertion inlet projecting from said sheath casing, the improvement comprising means for disengaging said sheath casing from said operating portion so as to rotate said sheath casing with respect to said operating portion and engaging said sheath casing to said operating portion so that said forceps inserting inlet is oriented at a desired angle.

* * * * *